United States Patent
Chang et al.

(10) Patent No.: US 10,813,887 B2
(45) Date of Patent: Oct. 27, 2020

(54) ACID RESISTANT CAPSULE SHELL COMPOSITION

(71) Applicant: DAH FENG CAPSULE INDUSTRY CO., LTD, Taichung (TW)

(72) Inventors: Ruei-Jan Chang, Taichung (TW); Yi-Huei Lin, Taichung (TW); Pei-Hsuan Lee, Taichung (TW); Hsin-Yi Chao, Taichung (TW)

(73) Assignee: DAH FENG CAPSULE INDUSTRY CO., LTD, Taichung (TW)

( * ) Notice: Subject to any disclaimer, the term of this patent is extended or adjusted under 35 U.S.C. 154(b) by 0 days.

(21) Appl. No.: 15/956,095

(22) Filed: Apr. 18, 2018

(65) Prior Publication Data

US 2019/0321301 A1    Oct. 24, 2019

(51) Int. Cl.
*A61K 9/48* (2006.01)

(52) U.S. Cl.
CPC .......... *A61K 9/4816* (2013.01); *A61K 9/4833* (2013.01)

(58) Field of Classification Search
None
See application file for complete search history.

(56) References Cited

U.S. PATENT DOCUMENTS

| | | | |
|---|---|---|---|
| 2003/0175335 A1* | 9/2003 | Scott | A61K 8/0216 424/452 |
| 2003/0206957 A1* | 11/2003 | Scherr | A61K 9/1652 424/488 |

FOREIGN PATENT DOCUMENTS

| | | |
|---|---|---|
| EP | 1315479 B1 | 11/2006 |
| EP | 3178473 A1 | 6/2017 |
| EP | 3205338 A1 | 8/2017 |
| JP | 2015189684 A | 11/2015 |

OTHER PUBLICATIONS

Search Report dated Sep. 23, 2019 issued by the European Patent Office for counterpart application No. 19169625.
English Abstract Machine Translation of Foreign Reference JP 2015189684A.
Office Action dated Jun. 15, 2020 issued by Taiwan Intellectual Property Office for counterpart application No. 108113539.
Search Report dated Jun. 15, 2020 issued by Taiwan Intellectual Property Office for counterpart application No. 108113539.
English Abstract Translation of Search Report issued by Taiwan Intellectual Property Office.

* cited by examiner

*Primary Examiner* — Robert A Wax
*Assistant Examiner* — Randeep Singh
(74) *Attorney, Agent, or Firm* — WPAT, P.C., Intellectual Property Attorneys; Anthony King

(57) ABSTRACT

The present disclosure provides an acid resistant capsule shell composition including pectin with a degree of esterification (DE) of about 15% to about 40%, and a degree of amidation (DA) of greater than 0% to about 25%; and a divalent cation. An acid resistant capsule shell and a method for manufacturing the acid resistant capsule shell are also provided in the present disclosure.

12 Claims, No Drawings

ACID RESISTANT CAPSULE SHELL COMPOSITION

BACKGROUND

1. Field of the Disclosure

The present disclosure relates to a composition, and more particularly to an acid resistant capsule shell composition.

2. Description of the Related Art

Generally, a capsule shell refers to a container enclosing medicines, such that the capsule, including the medicines and the shell, can be taken orally or be used as suppositories. There are two main types of capsule shells: soft capsule (single-piece gel encapsulation) shell and hard capsule (two-piece gel encapsulation) shell. Both of these types of capsule shells are made from aqueous solutions of film forming polymers, such as gelatin, starch and cellulose derivatives. The soft capsule shell is usually formed along with medicines (in a liquid form) to be enclosed, and the soft capsule shell is completely filled by the medicines. On the other hand, the hard capsule shell is initially formed without medicines and remains empty when supplying to the pharmaceutical manufacturer. Hence, the hard capsule shell requires stronger gelling strength.

After administration, the capsule shell dissolves, thus releasing the medicines enclosed therein. The contents of the capsule shell affect where the medicines are released. For example, a main component of a conventional capsule shell is gelatin, which is soluble in an acidic environment, such as a gastric condition. As a result, such conventional capsule shell comprising gelatin is dissolved in gastric acid, and the medicines enclosed therein are consequently released in the stomach. However, some kinds of medicines are enteric, which should remain enclosed without being released in the stomach. For example, release of nonsteroidal anti-inflammatory drugs in the stomach may cause serious gastric side effects such as damage of gastric mucosa, gastrorrhagia, or gastric perforation. To avoid the undesired side effects, the medicines should be enclosed in an enteric capsule shell. The contents of the enteric capsule shell should be undissolved in the acidic environment and should be dissolved in a basic or neutral environment, such as the intestine cavity.

The conventional enteric capsule shell usually comprises an enteric polymer, such as hydroxypropyl methyl cellulose acetate succinate (HPMCAS) or hypromellose phthalate (HPMCP); and a film forming polymer, such as starch or cellulose derivatives. In order to achieve good capsule shell formation and qualified gelling strength, a coagulant, such as gellan gum and carrageen, is necessary in the conventional enteric capsule shell. Such complicated composition complexes the manufacture of the enteric capsule shell, while the opportunity of undesired interactions between the medicines enclosed and the components of the enteric capsule shell is also raised.

In another aspect, the acid resistance of the conventional enteric capsule shell still fails to meet the requirement of the modern medicines. The conventional enteric capsule shell usually remains intact in a more acidic environment, such as about pH 1.2. However, the conventional enteric capsule shell starts to dissolve in a less acidic environment, such as about pH 3, which is covered by an acidity range in the normal stomach condition. As a reason, the conventional enteric capsule shell fails to enclose the medicine in the normal stomach condition.

In view of the deficiencies mentioned above, an enteric capsule shell with good capsule shell formation and qualified gelling strength as well as excellent acid resistance is needed to be provided in this field.

SUMMARY

An acid resistant capsule shell with good capsule shell formation and qualified gelling strength as well as excellent acid resistance is provided by a simple acid resistant capsule shell composition.

In some embodiments of the present disclosure, an acid resistant capsule shell composition includes pectin and a divalent cation. The pectin is provided with a degree of esterification (DE) of about 15% to about 40%, and a degree of amidation (DA) of greater than 0% to about 25%.

In some embodiments, the present disclosure further provides an acid resistant capsule shell including a body portion and a cap portion.

In some embodiments, the present disclosure further provides a method for manufacturing an acid resistant capsule shell, including:
(a) dissolving the acid resistant capsule shell composition as mentioned above in a solvent to form a solution;
(b) adhering the solution on a surface of a mold; and
(c) solidifying the solution to form a portion of the acid resistant capsule shell.

DETAILED DESCRIPTION

The present disclosure provides an acid resistant capsule shell composition, comprising:
pectin with a degree of esterification of about 15% to about 40%, and a degree of amidation of greater than 0% to about 25%; and
a divalent cation.

As used herein, the term "capsule shell" refers to a container enclosing medicines. A capsule including the medicines and the capsule shell can be taken orally or be used as suppositories. Preferably, "capsule shell" of the present disclosure refers to hard capsule shell for two-piece gel encapsulation.

As used herein, the term "acid resistant capsule shell" refers to a kind of capsule shell which is able to resist an acidic environment, such as gastric conditions, whilst would be readily dissolved under neutral environment, such as intestinal conditions. For example, the acid resistant capsule shell may have low dissolution rate under gastric conditions (about pH 1 to 3), such as lower than 15% for 2 hours, and is readily dissolved under intestinal conditions (about pH 6.8).

As used herein, the term "pectin", also known as pectic polysaccharide, refers to a structural heteropolysaccharide usually containing α-(1-4)-linked D-galacturonic acid group. In one embodiment of the invention, the pectin is extracted from the primary cell walls of terrestrial plants. Pectin presents in most primary cell walls and is particularly abundant in the non-woody parts of terrestrial plants. The amount, structure and chemical content of pectin differ among plants, within a plant over time, and in various parts of a plant. Therefore, various pectins with different chemical structures are extracted and obtained from the natural sources. In another embodiment of the invention, the pectin is artificially synthesized, and desired modifications to the structure are conducted by organically chemical procedures. The manners for extracting or artificial modifications are known to artisans skilled in this field.

In one embodiment of the invention, the pectin is rich in galacturonic acid and carboxyl groups of galacturonic acid are esterified, such as esterified with methanol. The ratio of esterified carboxyl groups to total carboxyl groups is termed as the degree of esterification (DE). According to the degree of esterification thereof, pectin can be classified as high-vs. low-ester pectin (HM vs. LM-pectin), with more or less than half of all the galacturonic acid esterified. In nature, the pectin comprises approximately 80% of esterified galacturonic acid. This proportion is decreased to a varying degree during pectin extraction. The pectin with the degree of esterification of about 15% to about 40% according to the invention can be obtained by the extraction process as well as directly esterifying the carboxyl groups of galacturonic acid. While not willing to be bound by any theory, it is believed that the degree of esterification determines the properties of pectin. On the other hand, the non-esterified carboxyl groups can be either free acids (carboxyl groups) or salts with sodium, potassium, or calcium.

In one embodiment of the invention, the pectin has acetylated galacturonic acid in addition to methyl esters. Such pectin can be found in some plants such as sugar beet, potatoes and pears contain. Amidated pectin is a modified form of pectin where some of the galacturonic acid is converted with ammonia to carboxylic acid amide. The degree of amidation (DA) is defined as the percentage of carboxyl groups that are in the amide form.

The composition of the acid resistant capsule shell (i.e., enteric capsule shell) according to the invention comprises the pectin acting as an enteric polymer to provide a pH-dependent dissolution. The enteric polymer such as the pectin according to the invention has low dissolution rate under gastric conditions (usually simulated by a pH value of about 1.2), such as lower than about 15% for about 2 hours, and is readily dissolved under intestinal conditions (usually simulated by a pH value of about 6.8). While not willing to be bound by any theory, it is believed that the degree of esterification and the degree of amidation cooperate to achieve excellent acid resistance. The gelling range for a LM-pectin is normally from about pH 2.6 to about pH 7.0. However, the pH value of gastric conditions may vary from about pH 1 to about pH 3. The LM-pectin with the gelling range from about pH 2.6 to about pH 7.0 may not remain undissolved under a pH of 3. To address at least the above concerns, the specific degree of amidation is provided in the pectin of the present disclosure.

In the present disclosure, we surprisingly found that such pectin provides the acid resistant capsule shell composition with low dissolution rate under both about pH 1.2 and about pH 3, such as less than about 15% for 2 hours. While not willing to be bound by any theory, it is believed that the specified amount of DE and DA jointly affect the enteric properties of the pectin. That is, it is the presence of such pectin provides the acid resistant capsule shell composition with the ability to remain undissolved under a pH as high as about 3. In some embodiments of the present disclosure, the acid resistant capsule shell composition is further provided with favorable gelling strength and capsule shell formation.

In some embodiments of the present disclosure, the degree of esterification of the pectin is preferably about 20% to about 35%, more preferably about 20% to about 30%.

In some embodiments of the present disclosure, the degree of amidation of the pectin is preferably about 10% to about 25%, more preferably about 15% to about 25%.

In addition, in some embodiments of the present disclosure, the content of the pectin in the acid resistant capsule shell composition is about 3% to about 30% by weight based on total solid content of the acid resistant capsule shell composition, preferably about 5% to about 25%, more preferably about 10% to about 20%.

If the pectin content is less than about 3%, the acid resistant capsule shell composition cannot form capsule shell due to its poor gelling strength, and the dissolution rate thereof is greater than about 15%. On the other hand, a pectin content greater than about 30% results in a huge viscosity, which adversely affect capsule shell formation.

In some embodiments, the acid resistant capsule shell composition comprises:
an enteric polymer, consisting of the pectin; and
the divalent cation.

The acid resistant capsule shell composition includes merely the pectin as the enteric polymer for providing a pH-dependent dissolution. That is, the acid resistant capsule shell composition may not include other enteric polymers. None of the other components of the acid resistant capsule shell composition has enteric properties. In some embodiments, an acid resistant capsule shell composition includes an enteric polymer which consists of pectin with a degree of esterification of about 15% to about 40%, and a degree of amidation of greater than 0% to about 25%; and a divalent cation.

The acid resistant capsule shell composition according to the invention includes a divalent cation. The divalent cation enhances the enteric properties of the pectin and gelling strength as well as capsule shell formation. In some embodiments of the present disclosure, the divalent cation is preferably non-toxic. For example, the divalent cation may be calcium ion ($Ca^{2+}$), magnesium ion ($Mg^{2+}$) and/or zinc ion ($Zn^{2+}$). Preferably, the divalent cation is selected from a group consisting of calcium ion and magnesium ion. While not willing to be bound by any theory, it is believed that ionic bridges are formed between the divalent cations and ionized carboxyl groups of the galacturonic acid in the pectin.

In some embodiments of the present disclosure, the divalent cation is provided by a divalent salt. The divalent salt is preferably soluble. For example, a solubility of the divalent salt may be greater than 0.1 g per 100 ml of solvent, preferably greater than 1 g per 100 ml of solvent, and more preferably greater than 10 g per 100 ml of solvent. In some embodiments of the present disclosure, the solvent may be water, preferably deionized water. Preferably, the anion of the divalent salt is also non-toxic. For example, the anion may be chloride ion ($Cl^-$).

In some embodiments of the present disclosure, a content of the divalent salt in the acid resistant capsule shell composition is about 0.05% to about 5% by weight based on total solid content of the acid resistant capsule shell composition. In the case that the content of the divalent salt is less than 0.05%, the dissolution of the acid resistant capsule shell composition under both about pH 1.2 and about pH 3 may increase, such as greater than about 15% for about 2 hours. On the other hand, if the content of the divalent salt is greater than about 5%, the acid resistant capsule shell composition cannot form capsule shell due to its huge viscosity.

In some embodiments of the present disclosure, the acid resistant capsule shell composition further includes a film-forming polymer. The term "film-forming polymer" refers to a polymer which is able to, or has the tendency to, form smooth and continuous film. Examples of the film-forming polymer include but are not limited to hydroxypropyl methylcellulose (HPMC), starch, gelatin, pullulan, polyvinyl alcohol, hydroxypropylated starch, hydroxyethylated starch, hydroxypropyl cellulose, methylcellulose, hydroxyethyl cellulose, and hydroxyethyl methyl cellulose. In some embodiments, the film-forming polymer excludes enteric polymers and/or coagulants. The film-forming polymer is preferably made or extract from a vegan source. Preferably, film-forming polymer is hydroxypropyl methylcellulose, starch (modified or unmodified), or pullulan.

In some embodiments of the present disclosure, the content of the film-forming polymer is 65% to 96.95% by weight based on total solid content of the acid resistant capsule shell composition; preferably about 70% to about 95%, more preferably about 75% to about 90%.

In some embodiments of the present disclosure, the acid resistant capsule shell composition consists essentially of:
the pectin;
the divalent cation; and
a film-forming polymer.

In some embodiments, the acid resistant capsule shell composition is free of coagulant. In a conventional enteric capsule shell composition, the coagulant is applied for the purpose of gelling strength improvement. As used herein, the term "coagulant" refers to a substance which increases the elasticity of a gel solution, and makes the gel solution transform from a viscous liquid state into an elastic solid state. Examples of the coagulant include but are not limited to gellan gum, carrageen, and sodium alginate. By incorporating the pectin and the divalent cation as well as the film-forming polymer, the acid resistant capsule shell composition is provided with good capsule shell formation and qualified gelling strength.

In some embodiments, the acid resistant capsule shell composition may further include surfactants, coloring agents, plasticizers and flavoring agents.

In some embodiments of the present disclosure, the acid resistant capsule shell composition may consist essentially of the pectin, the divalent cation (e.g., the divalent salt) and the film-forming polymer. The definition of "consist essentially of" does not exclude surfactants, coloring agents, plasticizers and flavoring agents. That is, the acid resistant capsule shell composition may additionally include at least one additional ingredient selected from the group consisting of coloring agents, plasticizers and flavoring agents According to the present disclosure, definition and determining method for "dissolution rate" may refer to United States Pharmacopeia 711 (USP <711>). In the present disclosure, dissolution of the acid resistant capsule shell composition is determined under about pH 1.2 and about pH 3, both stands for the gastric condition.

In some embodiments, a dissolution rate of the acid resistant capsule shell composition under an environment of about pH 1.2 for 2 hours is less than about 15%, preferably less than about 10%. A dissolution rate of the acid resistant capsule shell composition under an environment of about pH 3 for 2 hours is less than about 15%, preferably less than 10%.

The acid resistant capsule shell composition according to some embodiments of the present disclosure may be used in encapsulation of medicines. For example, the acid resistant capsule shell composition may forms hard capsule for enteric drug delivery. However, the application of the acid resistant capsule shell composition is limited thereto.

In some embodiments, the present disclosure further provides an acid resistant capsule shell, comprising:
a body portion; and
a cap portion;
wherein at least one of the body portion and the cap portion is made of the aforementioned acid resistant capsule shell composition.

The cap portion may seal the body portion. However, the body portion and the cap portion may both be made of the aforementioned acid resistant capsule shell composition. Such acid resistant capsule shell is a hard capsule shell for two-piece gel encapsulation.

In some embodiments, the present disclosure further provides a method for manufacturing an acid resistant capsule shell, comprising:

(a) dissolving the acid resistant capsule shell composition as mentioned above in a solvent to form a solution;

(b) adhering the solution on a surface of a mold; and (c) solidifying the solution to form a portion of an acid resistant capsule shell.

Preferably, the dissolving step (a) is conducted at about 40° C. to about 100° C. The solution is stirred at about 40° C. to about 100° C. to ensure the acid resistant capsule shell composition is completely dissolved.

In one preferred embodiment of the invention, the step (b) comprises dipping the mold into the solution, such that the solution is adhered to an outer surface of the mold.

In one preferred embodiment of the invention, after step (c), the method further comprising: (d) drying the portion of an acid resistant capsule shell. The portion of an acid resistant capsule shell may be dried at about 10° C. to about 80° C.

In one preferred embodiment of the invention, after step (d), the method further comprising: (e) separating the portion of an acid resistant capsule shell from the mold.

The following examples are given for the purpose of illustration only and are not intended to limit the scope of the present invention Table 1 shows the acid resistant capsule shell compositions of Examples 1 to 13 (abbreviated as E1 to E13 in Table 1) and Comparative Examples 1 to 6 (abbreviated as C1 to C6 in Table 1). In Table 1, 30-40% DE indicates that a distribution of the DE value of the pectin, preferably in normal distribution, is within the range of 30% to 40%. Similarly, 0-15% DA indicates that a distribution of the DA value of the pectin, preferably in normal distribution, is within the range of 0% to 15%. That is, a small portion of the pectin may have a DA value of 0, while most of the pectin has a DA value greater than 0. The exact distribution of the DE and DA values may vary slightly from batch to batch.

Each of the compositions of Examples 1 to 13 and Comparative Examples 1 to 6 was dissolved in a solvent. For example, 998.05 grams (g) of the composition were dissolved in 6.1 kilograms (kg) of deionized water to form a solution. The solution may be stirred under a temperature of about 80° C. to ensure the composition completely dissolved, and then cooled down to about 55° C. A capsule shell was then formed of the aforementioned solution by, for example, dip molding process, and was then dried at about 10 to about 80° C.

The properties of the capsule shells formed of the compositions of Examples 1 to 13 and Comparative Examples 1 to 6, including gelling strength, capsule shell formation condition and dissolution under pH 1.2 and pH 3 for 2 hours were recorded in Table 1.

TABLE 1

Composition E1 to E13 and C1 to C6, and Properties of capsule shell formed thereof

| No. | Pectin (wt %) | DE and DA of Pectin DE (%) | DE and DA of Pectin DA (%) | Divalent Salt (wt %) | Film forming polymer (wt %) | Gelling strength (g) | Capsule shell formation | Dissolution rate (2 hours) pH 1.2 | Dissolution rate (2 hours) pH 3 |
|---|---|---|---|---|---|---|---|---|---|
| E1 | 15 | 30-40 | 15-25 | 0.3% CaCl$_2$ | 84.7% HPMC | 9 | ◉ | 9.11% | 12.41% |
| E2 | 15 | 30-40 | 0-15 | 0.3% CaCl$_2$ | 84.7% HPMC | 8 | ◉ | 9.58% | 13.41% |
| E3 | 15 | 15-20 | 15-25 | 0.3% CaCl$_2$ | 84.7% HPMC | 14 | ◉ | 9.58% | 10.59% |
| E4 | 15 | 15-20 | 0-15 | 0.3% CaCl$_2$ | 84.7% HPMC | 10 | ◉ | 9.02% | 13.72% |
| E5 | 15 | 20-30 | 15-25 | 0.3% CaCl$_2$ | 84.7% HPMC | 11 | ◉ | 7.73% | 7.12% |
| E6 | 15 | 20-30 | 15-25 | 0.05% CaCl$_2$ | 84.95% HPMC | 6 | ○ | 14.95% | 14.97% |
| E7 | 15 | 20-30 | 15-25 | 5% CaCl$_2$ | 80% HPMC | 30 | ○ | 6.95% | 7.13% |
| E8 | 3 | 20-30 | 15-25 | 0.3% CaCl$_2$ | 96.7% HPMC | 8 | ○ | 13.98% | 14.85% |
| E9 | 30 | 20-30 | 15-25 | 0.3% CaCl$_2$ | 69.7% HPMC | 18 | ○ | 6.85% | 6.87% |
| E10 | 15 | 20-30 | 15-25 | 0.3% MgCl2 | 84.7% HPMC | 9 | ◉ | 9.68% | 9.77% |
| E11 | 15 | 20-30 | 15-25 | 0.3% CaCl$_2$ | 84.7% PULLULAN | 11 | ◉ | 7.81% | 7.89% |
| E12 | 15 | 20-30 | 15-25 | 0.3% CaCl$_2$ | 84.7% STARCH | 13 | ◉ | 7.58% | 7.66% |
| E13 | 15 | 20-30 | 0-15 | 0.3% CaCl$_2$ | 84.7% HPMC | 11 | ◉ | 8.12% | 9.56% |
| C1 | 15 | 40-50 | 5-15 | 0.3% CaCl$_2$ | 84.7% HPMC | 3 | ○ | 16.85% | 16.53% |
| C2 | 15 | 20-30 | 15-25 | 0.04% CaCl$_2$ | 84.96% HPMC | 7 | ○ | 20.00% | 20.50% |
| C3 | 15 | 20-30 | 15-25 | 5.1% CaCl$_2$ | 79.9% HPMC | N/A | X | N/A | N/A |
| C4 | 2 | 20-30 | 15-25 | 0.3% CaCl$_2$ | 96.7% HPMC | 3 | X | 16.30% | 25.80% |
| C5 | 35 | 20-30 | 15-25 | 0.3% CaCl$_2$ | 64.7% HPMC | N/A | X | N/A | N/A |
| C6 | 15 | 10-15 | 15-25 | 0.3% CaCl$_2$ | 84.7% HPMC | >30 | X | N/A | N/A |

In Table 1, the gelling strength is measured by, for example, a texture analyzer. The aforementioned solutions are stock at about 25° C. for about 20 minutes before measurement. The capsule shell formation is detected by visual inspection, while ◉ indicates the capsule shell formation is qualified as "good", while ○ indicates "acceptable" and X indicates "unacceptable." For example, ◉ indicates that the aforementioned solution forms smooth and continuous film on the mold pin without dripping; ○ indicates that the aforementioned solution forms smooth and continuous film on the mold pin with slightly dripping due to gravity; and X indicates the aforementioned solution drips from the mold pin thus cannot form continuous film. Among the examples, the acid resistant capsule shell compositions Comparative Examples 3, 5 and 6 (C3, C5 and C6) cannot form capsule shell due to extra-large viscosity thereof ("N/A" indicates "not applicable.").

As used herein, the terms "approximately," "substantially," "substantial" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified.

While the present disclosure has been described and illustrated with reference to specific embodiments thereof, these descriptions and illustrations are not limiting. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other embodiments of the present disclosure which are not specifically illustrated. The specification and drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations of the present disclosure.

What is claimed is:

1. An acid resistant capsule shell composition, comprising:
    pectin with a degree of esterification of about 15% to about 40%, and a degree of amidation of greater than 0% to about 25%; and
    a divalent cation;
    wherein the content of the pectin is about 3% to about 30% by weight based on total solid content of the acid resistant capsule shell composition, the divalent cation is provided by a divalent salt, and the content of the divalent salt is about 0.05% to about 5% by weight based on total solid content of the acid resistant capsule shell composition, a dissolution rate of the acid resistant capsule shell composition under an environment of about pH 1.2 for about 2 hours is less than about 15%, and a dissolution rate of the acid resistant capsule shell composition under an environment of about pH 3 for about 2 hours is less than about 15%.

2. The acid resistant capsule shell composition of claim 1, wherein the degree of esterification of the pectin is about 20% to about 30%, and the degree of amidation of the pectin is about 15% to about 25%.

3. The acid resistant capsule shell composition of claim 1, wherein the divalent cation is selected from a group consisting of calcium ion, magnesium ion and zinc ion.

4. The acid resistant capsule shell composition of claim 3, wherein the divalent cation is provided by a divalent salt selected from a group consisting of calcium chloride and magnesium chloride.

5. The acid resistant capsule shell composition of claim 1, further comprising a film-forming polymer selected from a group consisting of hydroxypropyl methylcellulose, starch, gelatin, pullulan, polyvinyl alcohol, hydroxypropylated starch, hydroxyethylated starch, hydroxypropyl cellulose, methylcellulose, hydroxyethyl cellulose, and hydroxyethyl methyl cellulose.

6. The acid resistant capsule shell composition of claim 5, wherein the content of the film-forming polymer is about 65% to about 96.95% by weight based on total solid content.

7. The acid resistant capsule shell composition of claim 1, which comprises:
    an enteric polymer, consisting of the pectin; and
    the divalent cation.

8. The acid resistant capsule shell composition of claim 1, which is free of coagulant.

9. The acid resistant capsule shell composition of claim 1, which consists essentially of:
    the pectin;
    the divalent cation; and
    a film-forming polymer.

10. The acid resistant capsule shell composition of claim 9, wherein the film-forming polymer is selected from a group consisting of hydroxypropyl methylcellulose, starch, gelatin, pullulan, polyvinyl alcohol, hydroxypropylated starch, hydroxyethylated starch, hydroxypropyl cellulose, methylcellulose, hydroxyethyl cellulose, and hydroxyethyl methyl cellulose.

11. The acid resistant capsule shell composition of claim 9, additionally comprising at least one additional ingredient selected from the group consisting of coloring agents, plasticizers and flavoring agents.

12. An acid resistant capsule shell, comprising:
    a body portion; and
    a cap portion;
    wherein at least one of the body portion and the cap portion is made of the acid resistant capsule shell composition of claim 1.

* * * * *